United States Patent [19]

Christy

[11] Patent Number: 5,683,378

[45] Date of Patent: Nov. 4, 1997

[54] ENDOSCOPIC WOUND ACCESS AND ANCHORING DEVICE METHOD

[76] Inventor: William J. Christy, 1325 Sunset Dr., Winter Park, Fla. 32789

[21] Appl. No.: 495,179

[22] Filed: Jun. 27, 1995

[51] Int. Cl.$^6$ ............................................. A61B 17/00
[52] U.S. Cl. ........................ 606/1; 606/108; 604/174; 604/264
[58] Field of Search .................... 606/1, 108, 185; 604/167, 169, 174, 178, 264

[56] References Cited

U.S. PATENT DOCUMENTS

| | | | |
|---|---|---|---|
| 4,623,348 | 11/1986 | Feit | 604/264 |
| 4,675,006 | 6/1987 | Hrushesky | 604/174 |
| 4,781,703 | 11/1988 | Walker et al. | 604/264 |
| 4,838,877 | 6/1989 | Massau | 604/264 |
| 4,921,479 | 5/1990 | Grayzel | 606/108 |
| 5,176,662 | 1/1993 | Bartholomew et al. | 604/180 |
| 5,250,033 | 10/1993 | Evans et al. | 604/167 |
| 5,295,657 | 3/1994 | Atkinson | 604/167 |
| 5,304,183 | 4/1994 | Gourlay et al. | 505/151 |
| 5,322,516 | 6/1994 | Brugger | 604/264 |
| 5,364,367 | 11/1994 | Banks et al. | 604/174 |
| 5,366,446 | 11/1994 | Tal et al. | 604/110 |
| 5,366,478 | 11/1994 | Brinkerhoff et al. | 604/167 |
| 5,370,625 | 12/1994 | Shichman | 604/174 |
| 5,375,588 | 12/1994 | Yoon | 604/180 |
| 5,441,487 | 8/1995 | Vedder | 604/169 |
| 5,490,843 | 2/1996 | Hildwein et al. | 606/185 |

*Primary Examiner*—Michael Buiz
*Assistant Examiner*—Patrick W. Rasche
*Attorney, Agent, or Firm*—Allen, Dyer, Doppelt, Milbrath & Gilchrist, P.A.

[57] ABSTRACT

A tapered cannula is provided for maintaining gas pressure within a body cavity during an intracavity procedure. The cannula is long enough to penetrate into the body cavity and has an exterior diameter tapering downward from the proximal end to the distal end. In use the cannula is inserted sufficiently far that the cannula creates a leakproof seal with incision. Another device is provided that serves a similar purpose, except that it does not extend into the body cavity. This device has the added feature of providing a platform that is anchorable to surrounding skin.

8 Claims, 5 Drawing Sheets

ENDOSCOPIC WOUND ACCESS AND ANCHORING DEVICE METHOD

BACKGROUND OF THE INVENTION

1. Field of the Invention

This invention relates generally tot he field of surgical devices and, more particularly, to surgical cannula devices used as portals to body cavities in laparoscopic and endoscopic applications.

2. Description of Related Art

Laparoscopic or endoscopic surgical procedures are now widely used in many specialties in the surgical community. These procedures generally involve a "C"-shaped incision through the navel, through skin, adipose tissue, fascia, muscle, and peritoneum, which comprise the abdominal wall or thoracic wall. Using this method many organs of the gut may be viewed and operated upon: gall bladder, intestines, appendix, uterus, fallopian tubes, ovaries, and lungs.

Trocars, pointed cannulae with pointed obturators for piercing the wall of a cavity, are often used to create ports through which surgical instruments may be passed, instead of making long incisions in the abdominal or thoracic wall. The diameter of the trocar differs based upon the procedure to be performed, and may range from 3 to 33 millimeters.

Once the puncture has been made, the pointed trocar is usually removed, and the cannula is then utilized as a port through which instruments and viewing devices may be passed into the body cavity.

Laparoscopic or endoscopic procedures generally entail the introduction of elevated-pressure gas into the body cavity being operated upon. This enables the surgeon to visualize the area better and also provides additional room in which to work. Significant leakage of gas pressure would cause the area to collapse, disturbing and delaying the procedure, which could be dangerous. Such a leakage can occur, for instance, during a change of instruments through a cannula or trocar, or during suturing, after a trocar has been removed.

It is known to use a gasket at the proximal end of a cannula to prevent loss of pressure; however, gas may also leak out from around the exterior of the cannula.

Another difficulty in procedures such as those involving multiple cannulae is that one may be easily disturbed while moving about the external area.

Several trocar stabilizers are known in the art, including those taught by Banks et al. (U.S. Pat. No. 5,364,36), Tal et al. (U.S. Pat. No. 5,366,446), Brinkerhoff et al. (U.S. Pat. No. 5,366,478), Shichman (U.S. Pat. No. 5,370,625), and Yoon (U.S. Pat. No. 5,375,588).

SUMMARY OP THE PRESENT INVENTION

It is an object of the present invention to provide a cannula device for use in endoscopic and laparoscopic procedures that maintains gas pressure within a body cavity during a surgical procedure.

It is another object to provide such a device that is anchorable to an external area of the surgical site.

It is a further object to provide a method of operating upon a body cavity while maintaining a desired gas pressure within that cavity.

These and other objects are achieved with the following embodiments of the invention.

Device for Maintaining Gas Pressure within a Body Cavity: Embodiment 1

The present invention comprises a device for maintaining gas pressure within the body cavity during an intracavity procedure. In a first embodiment this device comprises a tapered cannula for maintaining gas pressure within the body cavity. The cannula has a proximal end, a distal end, and a longitudinal bore extending from the proximal end to the distal end and having a width dimensioned to permit passage of a desired surgical implement therethrough. The cannula further has a length sufficient to penetrate into the body cavity. The cannula additionally has an exterior diameter tapering downward from the proximal end to the distal end.

In use the distal end of the cannula is inserted into an incision into the body cavity sufficiently far to extend into the body cavity and also sufficiently far that the cannula creates a leakproof seal with the incision, thus maintaining gas pressure within the cavity.

Device for Maintaining Gas Pressure within the Body Cavity Embodiment 2

The present invention further comprises in a second embodiment an alternate means of maintaining gas pressure within the body cavity. In this embodiment the device comprises a generally cylindrical body having a proximal end, a distal end, and a longitudinal bore extending from the proximal end to the distal end, the bore being dimensioned to admit a surgical suturing implement thereinto.

The cylindrical body further has a length sufficient to penetrate a predetermined distance into the incision, but generally into the fat layer, and preferably into the anterior fascia layer. If the device is used with a trocar, the length is sufficient to penetrate all the way into the incision.

The device further comprises a lip at the cylindrical body's proximal end. This lip is dimensioned to restrain the proximal end from entering the incision.

Affixed within the bore are sealing means. The sealing means has a perforation that is expandable to admit and closely surround the surgical implement. In this way, when the implement is inserted into the incision through the device, gas pressure is maintained.

In a preferred embodiment the lip comprises means affixed adjacent the proximal end of the cylindrical body for anchoring it to skin surrounding the incision.

Method for Maintaining Gas Pressure within a Body Cavity during a Surgical Procedure: Embodiment One As mentioned in the Background section, certain types of surgery are performed within body cavities that have been pressurized, essentially blowing up the area like a balloon. Obviously, in order to maintain this pressure, the area must be maintained as leakproof as possible. In the case of peritoneal surgery, for instance, in which carbon dioxide pressure is introduced to improve visualization of the operating site by the surgeon, the opening of an incision can cause loss of the pressure, collapsing the area being operated upon.

In one embodiment of the present invention, the tapered cannula described previously can be utilized to maintain gas pressure within a body cavity during the surgical procedure. In this method, the tapered cannula is inserted into the narrow incision sufficiently far to create a leakproof seal with the incision. Next a surgical implement is inserted into the cannula, and the desired surgical procedure is performed with the surgical implement.

Method for Maintaining Gas Pressure within a Body Cavity during a Surgical Procedure: Embodiment Two A second embodiment of the method for maintaining gas pressure in a body cavity during a surgical procedure comprises the steps of inserting the device described above into the incision.

Next the device is anchored against the skin surrounding the incision, and a surgical implement is inserted into the bore of the device. With the device sealing the body cavity off from the atmosphere, the surgical procedure can be performed with the surgical implement in the device.

As an alternative, a cannula may be inserted into the bore of the device, in which case the surgical implement is inserted into the cannula. In this case it is preferable that the cannula also have sealing means for maintaining the body cavity gas pressure.

BRIEF DESCRIPTION OF THE DRAWINGS

A preferred embodiment of the invention along with alternate embodiments are described by way of example with reference to the accompanying drawings, in which:

FIG. 6 shows the device anchorable with pincers, with the elements in the (a) open and (b) closed positions. (c) pincers are restrained by a second annulus having slots shaped to permit opening, release, and reopening. (d) A plan view of the second annulus showing details of one of the slots therein.

FIG. 7 shows the device anchorable with complementary pairs of barbs depending from coaxial rings, the device shown in (a) side view; (b) plan view; and (c) bottom view. (d) Means for protecting the user against accidental injury from the barb points are shown that include a third circumferential ring movably affixed to the first ring. (e) This embodiment has windows permitting access to tissue surrounding the incision and to the edges of the incision.

FIG. 8 shows the method of using the tapered cannula, including the steps of (a) inserting the cannula into the incision, and (b) inserting a surgical implement into the cannula.

FIG. 9 shows the method of using the device, which includes (a) inserting the device into the incision and anchoring it against the skin; and (b) inserting and using a surgical implement. An alternate embodiment includes (c) inserting a cannula into the device bore; and (d) inserting the surgical implement into the cannula.

DETAILED DESCRIPTION OF THE PREFERRED EMBODIMENT

A description of the preferred embodiments of the present invention will now be presented with reference to FIGS. 1–9. All embodiments, both devices and methods, are directed to the maintenance of gas pressure within a body cavity during an intracavity procedure conducted through a narrow incision.

Device for Maintaining Gas Pressure within a Body Cavity: Tapered Cannula Embodiment This embodiment of the device of the present invention comprises a tapered cannula 10, shown in FIGS. 1 and 2. The cannula 12 has a proximal end 102, a distal end 104, and a length 106 sufficient to penetrate into the body cavity. The cannula 10 further has a longitudinal bore 108 extending from the proximal end 102 to the distal end 104 that has a width 110 dimensioned to permit passage of a desired surgical instrument therethrough.

Figure 1:
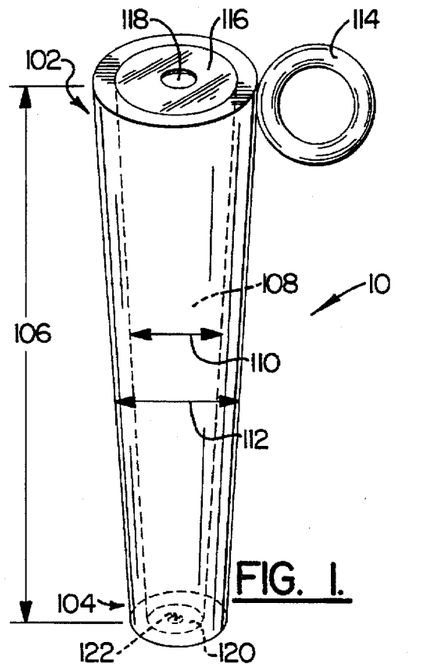
FIG. 1 illustrates the unitary tapered cannula having a perforated gasket.

Cannula 10 additionally has an exterior diameter 112 tapering downward from the proximal end 102 to the distal end 104.

In order to facilitate grasping the cannula 10 and further to prevent the cannula proximal end 102 from penetrating the incision, a handle 114 affixed to the proximal end 102 is also provided.

In use the distal end 104 of the cannula 10 is inserted into an incision into the body cavity sufficiently far to extend into the body cavity and also sufficiently far that the cannula 10 creates a leakproof seal with the incision, thus maintaining gas pressure within the cavity.

In one embodiment of the tapered cannula deformable sealing means 116 are affixed at the proximal end 102. The sealing means 116, which typically comprise a gasket of a material such as Latex™, has a perforation 118 expandable to admit and closely surround a surgical implement. In this way, when a surgical implement is inserted into the cannula bore 108, gas pressure is maintained.

Additionally, a second deformable sealing means 120 may be provided at the distal end 104. As with the first sealing means 116, the second sealing means 120 has a perforation 122 expandable to admit and closely surround a surgical implement.

Perforations 118 and 122 may take the form of a single slit, an "X"-shaped slit, or a small hole. Generally the perforations 118 and 122 should be expandable to 12 mm.

Figure 2:
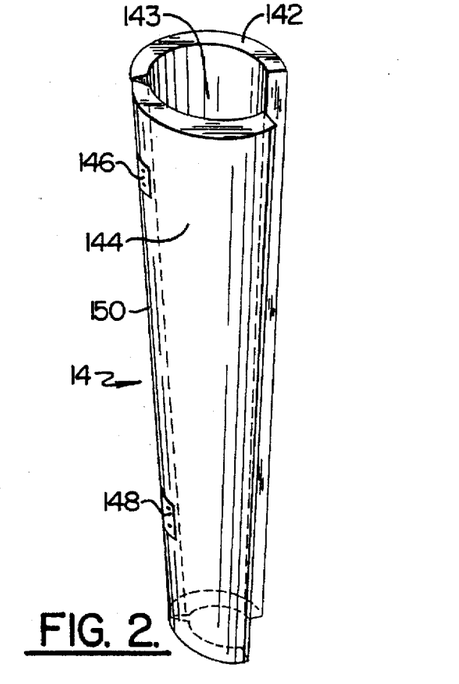
FIG. 2 illustrates the longitudinally hinged tapered cannula.

In another embodiment, shown in FIG. 2, a tapered cannula 14 consists of two matable longitudinal halves 142 and 144 and openable securing means for mating the halves 142 and 144. This securing means serves to permit movement between an open position for admitting a surgical implement and a closed position for surrounding the surgical implement within the cannula bore 143.

In one embodiment the securing means comprises hinge means, shown here as two hinges 146 and 148 affixed along a first side 150 of the cannula 14. Typically the hinges 146 and 148 will biased to retain the two halves 142 and 144 in the closed position.

This particular embodiment is utilized in situations wherein a particular surgical implement will reside and will be manipulated within the cannula 14 during a predetermined part of the procedure.

Device for Maintaining Gas Pressure within the Body Cavity

This embodiment of the device 20 has several alternate subembodiments illustrated in FIGS. 3–7. This device in its broadest aspect comprises a generally cylindrical body 22 that has a proximal end 222, a distal end 224, and a length 226 sufficient to penetrate a predetermined distance into an incision into the body cavity, but insufficient to penetrate into the body cavity. (In other embodiments the length is sufficient to penetrate into the wound, for instance, when used with a trocar.) Cylindrical body 22 further has a longitudinal bore 228 extending from the proximal end 222 to the distal end 224, which is dimensioned to admit a surgical implement thereinto.

Figures 3, 4, 5:
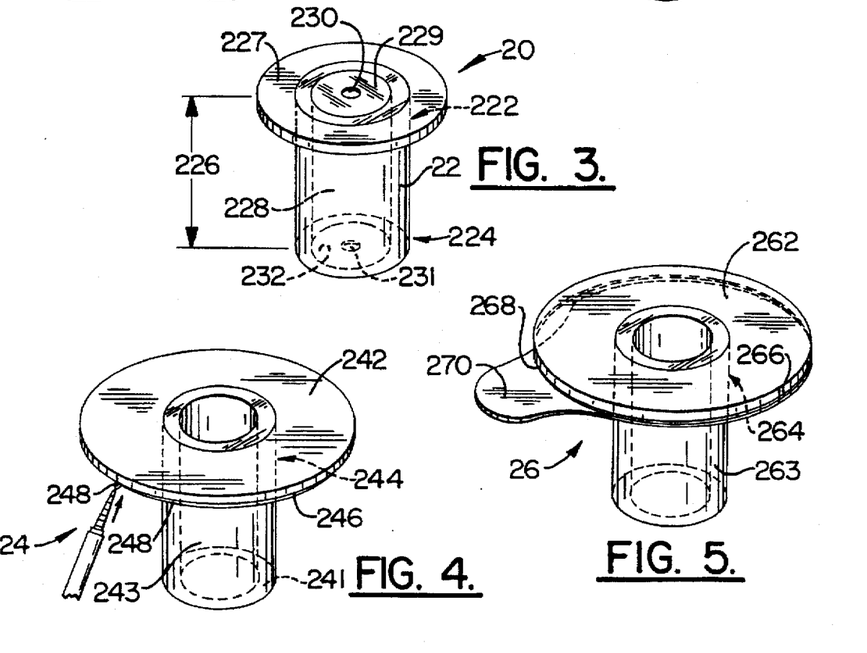
FIG. 3 shows the device having a lip.
FIG. 4 shows the device having a patch affixable with glue.
FIG. 5 shows the device having a patch affixable with adhesive.

Device 20 also has a lip 227 affixed adjacent the cylindrical body proximal end 222, as illustrated in FIG. 3. This lip 227 is dimensioned to restrain the cylindrical body proximal end 222 from entering the incision.

In order to maintain gas pressure during insertion of the surgical implant into the incision, sealing means are also provided. In a preferred embodiment, this comprises a gasket 229 affixed within the cylindrical body bore 228, typically adjacent the cylindrical body proximal end 222. The gasket 229 has a perforation 230 that is expandable to admit and closely surround the surgical implement.

In another embodiment, the device 22 additionally comprises a second gasket 232 affixed at the cylindrical body distal end 224. Second gasket 232 also has a perforation 231 that is expandable to admit and closely surround the surgical implement.

Another feature of a preferred embodiment of device 22 is an element that permits the device 22 to be affixed to an area of skin surrounding the incision. This enables the surgeon to manipulate surgical implements within the device and to insert and remove them without dislodging the device from the incision. Specifically, the lip 226 comprises means for anchoring the cylindrical body proximal end 222 to the skin.

Four devices having subembodiments of the anchoring means will be presented in the following.

Annular Patch with Glue. In this embodiment, shown in FIG. 4, the device 24 has anchoring means comprising an annular patch 242 affixed in surrounding relation to the cylindrical body 243 proximal end 244 having a distal surface 246 adapted to receive a glue 248 suited for attachment to the skin.

Annular Patch with Adhesive. In this embodiment, shown in FIG. 5, the device 26 has anchoring means comprising an annular patch 262 affixed in surrounding relation to the cylindrical body 263 proximal end 264 having an adhesive material 266 applied to a distal surface 268 for attachment to the skin.

Additionally, this embodiment may further comprise a removable protective sheet 270 covering the adhesive material 266 for shielding the adhesive material 266 until attachment to the skin in desired.

Pincers. In this embodiment, shown in FIG. 6, the device 28 has anchoring means comprising pincer means affixed to and protruding through an annular patch 280 that is affixed in surrounding relation to cylindrical body proximal end 264. The pincer means are here shown as a pair of generally opposed pincer elements 282 and 283, each having a pair of pointed tips 284 and 285, respectively. These pincer elements 282 and device in a similar manner to a clothespin or clamp, being movable between an open position [FIG. 6(a)] for insertion into the skin and a closed position [FIG. 6(b)] for pinching the skin. As with a clamp, the pincer elements 282 and 283 are biased to the closed position.

Figure 6A:
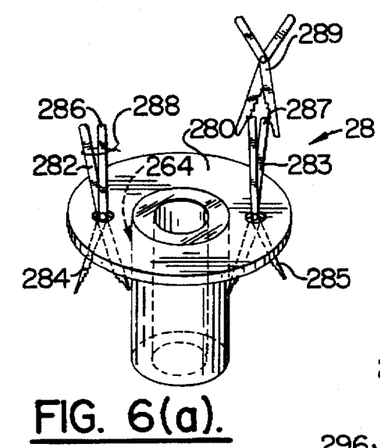
Figure 6B:
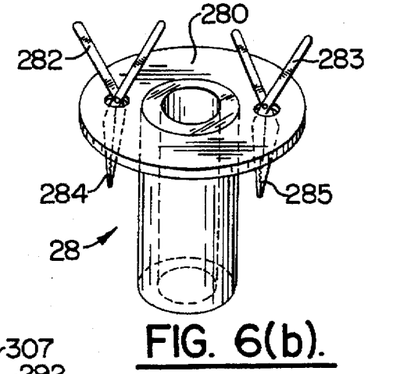

In a particular embodiment, the anchoring means of device 28 further has releasable means for restraining the pincer means in the open position. This feature permits the user to engage the restraining means during insertion of the pincer means into the skin and to release it after insertion, thereby permitting the pincer means to move to the closed position for pinching the skin when desired.

Specifically, the restraining means could comprise a means of keeping the pincer element tops 286 and 287 closely opposed, such as a tie 288 or a clamp 289, as shown in FIG. 6(a).

Figure 6C:
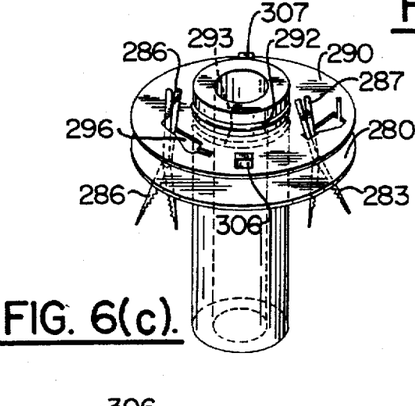
Figure 6D:
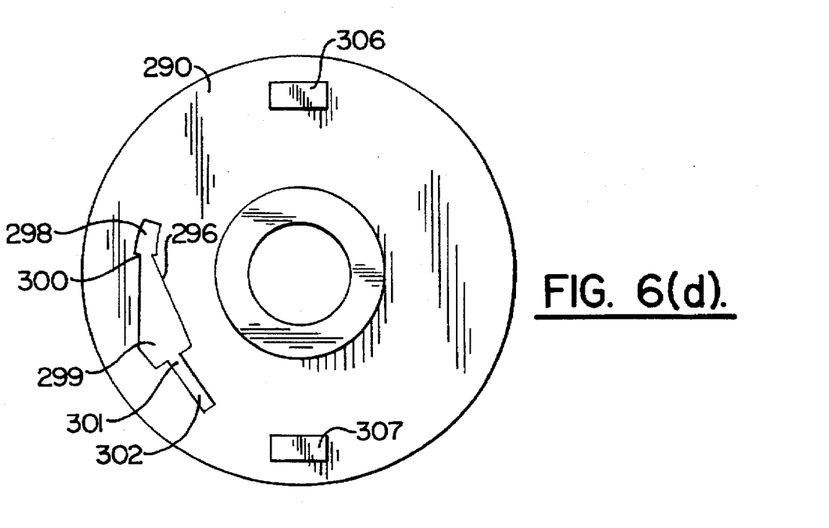

In another embodiment of the restraining means, shown in FIG. 6(c), a second annular patch 290 is rotatably affixed in spaced relation above annular patch 280 between first and second shoulders 292,293 on cylindrical body 22. Second annular patch 290 has slots 296 therethrough having a first end 298 dimensioned to restrain pincer element tops 286, 287 together, preventing pincer element tips 284,285 from closing [see FIG. 6(d), showing details of a slot 296]. Slots 296 further have a central section 299 dimensioned to permit pincer element tops 286,287 to open and thereby to permit pincer element tips 284,285 to close. In use, therefore, anchoring is accomplished by pressing second annular patch 290 until pincer element tips 284,285 penetrate the skin surrounding the incision, and then rotating second annular patch 290 to release the tops 286,287, which allows the tips 284,285 to spring together, pinching the skin. Rotation may be facilitated by upwardly extending protrusions 306,307, against which in use the thumb and forefinger would be placed to rotate second annular patch 290 in a desired direction.

An additional feature is provided to prevent the accidental release of the pincer elements 282,283. Slots 296, in proceeding from the first end 298 to central section 299, have a narrowed region 300 dimensioned smaller than first end 298, for providing a potential energy barrier to the pincer element tops 286,287 moving into the slot's central section 299 prematurely. This barrier is dimensioned to be able to be overcome by finger pressure forcibly rotating the second annular patch 290. Finally, when removal is desired, second annular patch 290 is rotated yet further, ramping pincer element tops 286,287 past second narrowed region 301 into slot second end 302, which is dimensioned sufficiently small to move the pincer elements 282,283 into the open position and permitting them to be removed from the skin.

Figure 7A:
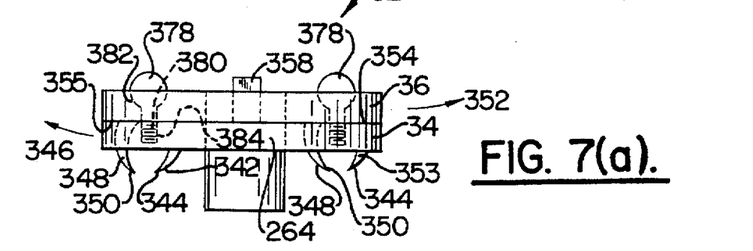
Figure 7B:
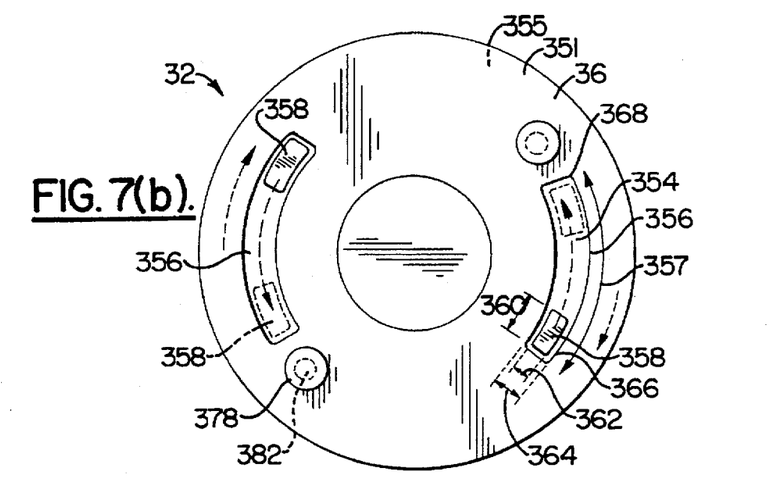
Figure 7C:
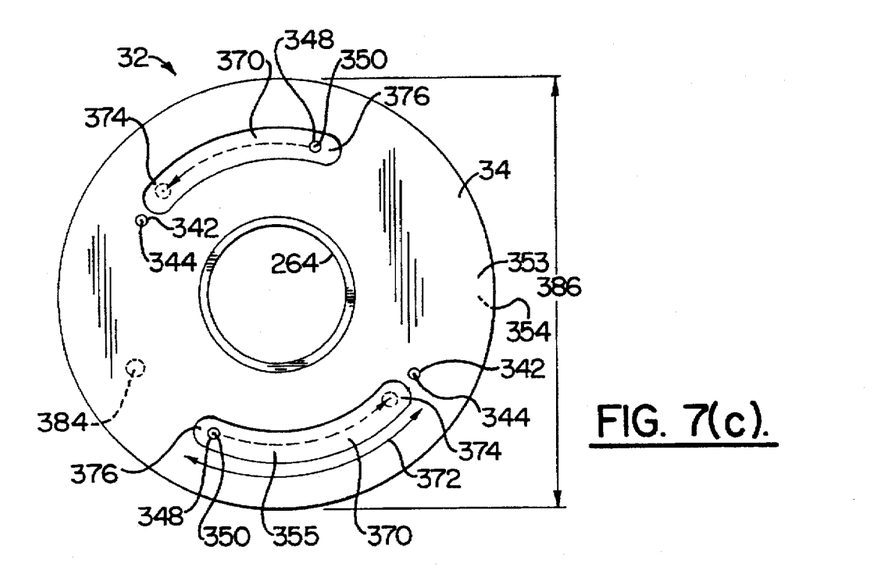

Opposable Barbs. In this embodiment, shown in FIG. 7(a–c), the device 32 has anchoring means comprising barb means protruding in a distal direction from adjacent the lip 322.

In a specific embodiment, the anchoring means comprises a first ring 34 and a second ring 36. First ring 34 is affixed in surrounding relation adjacent the cylindrical body proximal end 264. The first ring 34 has a first set of barbs 342 having points 344 protruding generally in a distal direction from the distal surface 353. The barbs 342 are canted generally in a first circumferential direction 346 (here, clockwise) with respect to the first ring 34.

Second ring 36 is adapted to engage the first ring 34 rotatably relative thereto. The second ring 36 comprises a second set of barbs 348 having points 350 protruding generally in a distal direction from distal surface 355. The barbs 348 are canted generally in a second circumferential direction 352 (here, counterclockwise) with respect to the second ring 36. Each one of the first set 342 has a complementary one of the second set 348 to form a pair of barbs having their points 344,350 generally opposed. The second ring 36 is further lockable in a position wherein the point 344 of a one barb of the first set 342 is generally adjacent the point 350 of a complementary barb of the second set 348.

In use the first 342 and the second set 348 of barbs are pushed into the skin surrounding the incision, the second ring 36 is rotated to move each one of the complementary pair of barbs adjacent each other, each pair of barbs pinching the skin therebetween, and the second ring 36 is locked to effect anchoring.

In a specific embodiment, first 34 and second 36 rings have opposed camming surfaces 354 and 355, respectively, that represent the proximal 354 and distal 355 surfaces, respectively. Protrusions 358 extending above first ring proximal surface 354 have complementary circumferential slots 356 through second ring 36, the slots 356 dimensioned to have a longer arc length 357 than the length 360 of protrusions 358. The protrusions 358 are dimensioned to have a width 362 closely slidable within the width 364 of slots 356 so that little radial movement is permitted therebetween. In this way first 34 and second 36 rings are relatively rotatable between a first position in which the protrusions 358 are positioned at a first end 366 of the slots 356 and a second position in which the protrusions 358 are positioned at a second end 368 of the slots 356.

First ring 34 further has circumferential slots 370 therethrough, these being offset from second ring slots 356 so as to avoid overlapping second ring slots 356 in either the first or the second position. In the embodiment shown both sets of circumferential slots 356,370 lie generally along a common circumference, although this is not necessary. First ring slots 370 have an arc length 372 generally the same as second ring slot arc length 357.

The first set of barbs 342 distally depend from first ring distal surface 353 and are positioned generally adjacent second ends 374 of slots 370. The second set of barbs 348 distally depend from second ring distal surface 355 and are positioned so as to be generally adjacent first ends 376 of slots 370 when the rings 34,36 are in the first position and further so as to be generally adjacent second ends 374 of slots 370 when the rings 34,36 are in the second position. Therefore, when the rings are rotated from the first to the second position, shown by dotted arrows in FIGS. 7(b) and (c), the herb points 344,350 go from being apart to being closely opposed.

In order to facilitate the relative rotation of rings 34,36, handle means are provided on the second ring proximal surface 351. Specifically, handle means comprise a pair of generally radially opposed upwardly extending knobs 378 that, when pushed, effect the desired rotation.

As mentioned, means are provided for locking the rings 34,36 against rotation when in the second position. This may be accomplished, in one embodiment, by having at least one of the knobs 378 further comprise a distally extending screw 380 that metes with a threaded bore 382 through second ring 36. When the rings 34,36 are in the second position, second ring threaded bore 382 communicates with first ring threaded bore 384, and, by screwing knob 378 beyond bore 382 into bore 384, locking between the rings 34,36 is effected.

Figures 7D, 7E, 8A, 8B:
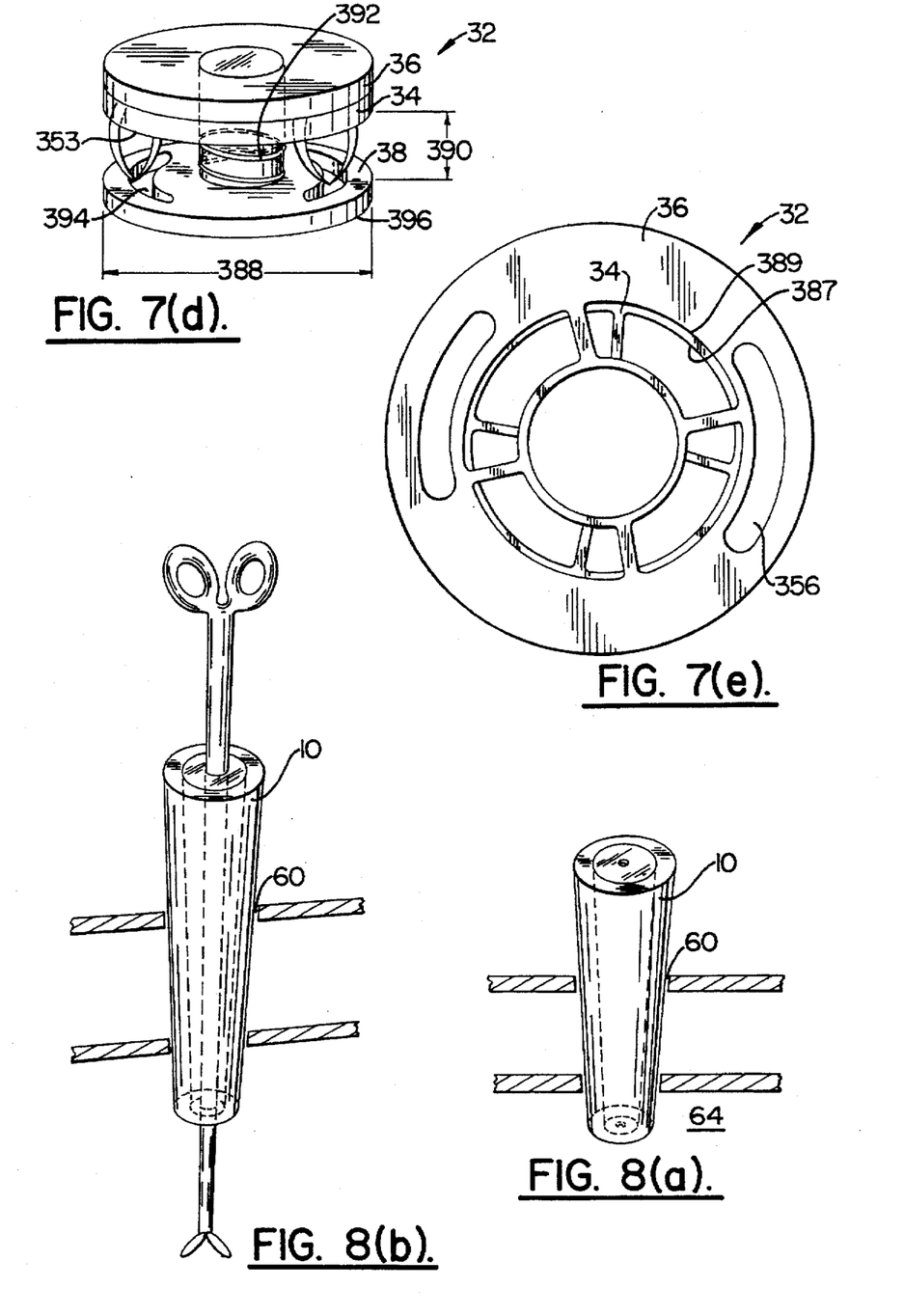

In order to prevent barb points 344,350 from injuring the user, the anchoring means further comprises releasable protective means for covering the barb points 344,350 until use is desired. In a simple embodiment, device 32 may be parked in a foam-type holder until needed. Another embodiment, however, is contemplated in which the protective means is a part of the device 32.

In this embodiment, shown in FIG. 7(d), a third ring 38 is provided that is movably affixed in spaced relation to first ring 34 and that has a diameter 388 generally the same as the diameter 386 of first ring 34. Third ring 38 is biased via spring 392, which is affixed at one end to first ring 34 and at another end to third ring 38, to be axially separated from first ring 34 by a distance at least equal to the axial extent 390 of the barbs 342,348 in a distal direction from the first ring distal surface 353.

Third ring 38 additionally has circumferential slots 394 therethrough that have an arc length at least sufficient to permit barbs 342,348 to protrude therethrough, as shown in FIG. 7(d). A compression of spring 392, to bring first 34 and third 38 rings into proximity, thus exposes the barb points 344,350, permitting them to be inserted into skin. In use, then, a release of the protective means, the third ring 38, is accomplished by placing the third ring distal surface 396 against the skin and pushing down on second ring 36, causing spring 392 to compress, permitting barbs 342,348 to protrude through third ring slots 294, and then to enter the skin.

In a subembodiment, cylindrical body 22 is sufficiently long to penetrate into the incision, and can itself act as a trocar.

In order to provide access through the device 32, the first ring 34 has four windows 387 therethrough from the proximal 353 to the distal 354 surface; similarly, the second ring 36 has four windows 389 therethrough from the proximal 351, to the distal 355 surface [see FIG. 7(e)]. Windows 387,389 are positioned to communicate at least partially, whether the first 34 and the second 36 rings are in the first or the second position. These windows are for permitting access to the tissue surrounding the incision and to the sides of the incision, providing the possibility of manipulating implements therethrough.

Method for Maintaining Gas Pressure within a Body Cavity: Tapered Cannula Embodiment The method for maintaining gas pressure in a body cavity 64 during a surgical procedure that uses a narrow incision 60 for access into the body cavity 64, as shown in FIG. 8, comprises inserting a tapered cannula 10 such as described above into the narrow incision 60 sufficiently far to create a leakproof seal with the incision 60 [FIG. 8(a)].

A surgical implement 62 is then inserted into the cannula 10, and the surgical procedure is performed with the surgical implement 62 [FIG. 8(b)].

Method for Maintaining Gas Pressure within a Body Cavity: Alternate Embodiment

Figure 9A:
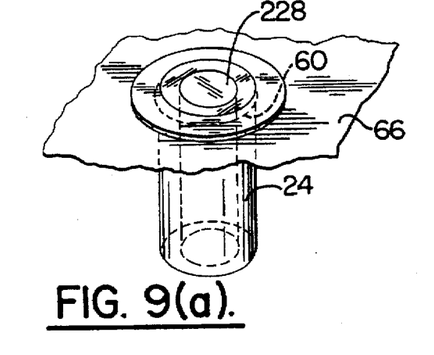
Figure 9B:
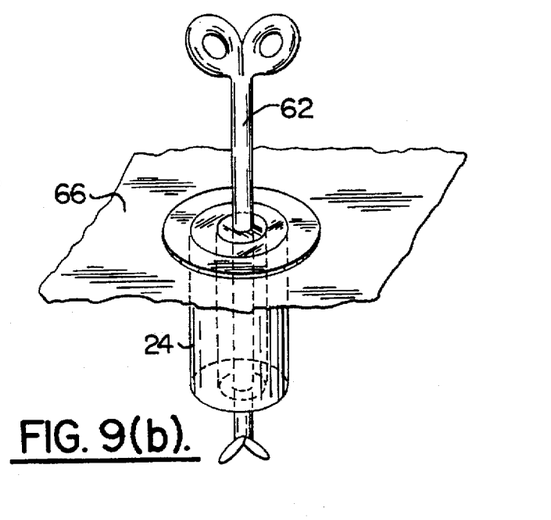

The method utilizing a device 24, as shown in FIG. 9, comprises inserting the device 24 into the incision 60 and anchoring it against skin 66 surrounding the incision 60 [FIG. 9(a)]. Next a surgical implement 62 is inserted into the device bore 228, and the surgical procedure is performed with the surgical implement 62 [FIG. 9(b)].

Figure 9C:
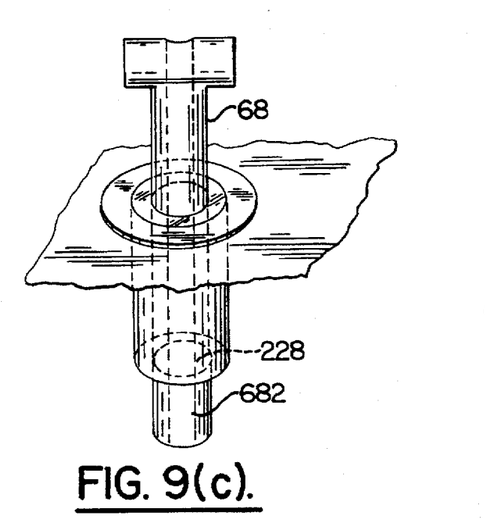
Figure 9D:
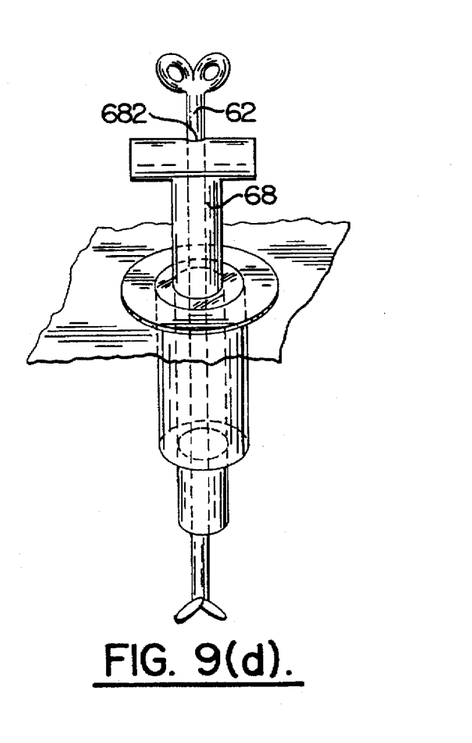

A related embodiment has the additional step, following the anchoring step, of inserting a cannula 68 into the device bore 228 [FIG. 9(c)], and wherein the surgical implement inserting step comprises inserting the surgical implement into the cannula bore 682 [FIG. 9(d)].

It may be appreciated by one skilled in the art that additional embodiments may be contemplated, including other means of deploying and positioning the suture needle and other methods for using the apparatus.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for maintaining gas pressure within the body cavity during an intracavity procedure, the device comprising:

a generally cylindrical body having:
        a proximal end;
        a distal end; and
        a longitudinal bore extending from the proximal end to the distal end, the bore dimensioned to admit a surgical implement thereinto; and means for anchoring the cylindrical body proximal end to skin surrounding the incision, the anchoring means dimensioned to restrain the cylindrical body proximal end from entering the incision and comprising:

a first ring affixed in surrounding relation adjacent the cylindrical body proximal end, the first ring comprising a first set of barbs having points protruding generally in a distal direction therefrom, the barbs canted generally in a first circumferential direction with respect to the first ring; and a second ring adapted to engage the first ring rotatably relative thereto, the second ring comprising a second set of barbs having points protruding generally in a distal direction therefrom, the barbs canted generally in a second circumferential direction with respect to the second ring, each one of the first set having a complementary one of the second set to form a pair of barbs, the second ring lockable in a position wherein the point of one barb of the first set is generally adjacent the point of a complementary barb of the second set;

wherein in use the first and the second set of barbs are pushed into the skin surrounding the incision, the second ring is rotated to move each one of the complementary pair of barbs adjacent each other, each pair of barbs pinching the skin therebetween, and the second ring is locked to effect anchoring.

2. The device recited in claim 1, wherein the anchoring means further comprises releasable protective means for covering the barb points until use is desired.

3. The device recited in claim 2, wherein the protective means comprises a third ring movably affixed in spaced relation beneath the first ring, the third ring having a plurality of slots therein aligned with the first and the second set of barbs, the third ring movable between a protective position distal of the first and the second set of barbs and an anchoring position proximal of the first and the second set of barbs, the first and the second set of barbs thereby protruding through the slots.

4. The device recited in claim 3, wherein the third ring is biased to the protective position.

5. The device recited in claim 4, further comprising spring means affixed at a first end to the first ring and at a second end to the third ring, the spring thereby biasing the third ring to the protective position.

6. The device recited in claim 1, wherein the anchoring means further comprises handle means affixed to the second ring for facilitating the rotation of the second ring during use.

7. The device recited in claim 8, wherein the window in the first ring and the window in the second ring each comprises a plurality of semiannular windows arrayed in surrounding relation to the cylindrical body.

8. A device for maintaining gas pressure within the body cavity during an intracavity procedure, the device comprising:

a generally cylindrical body having:
  a proximal end;
  a distal end; and
  a longitudinal bore extending from the proximal end to the distal end, the bore dimensioned to admit a surgical implement thereinto;

a lip affixed adjacent the cylindrical body proximal end dimensioned to restrain the cylindrical body proximal end from entering the incision; and means for anchoring the cylindrical body proximal end to skin surrounding the incision comprising:

a first ring affixed in surrounding relation adjacent the cylindrical body proximal end, the first ring comprising a first set of barbs having points protruding generally in a distal direction therefrom, the barbs canted generally in a first circumferential direction with respect to the first ring, the first ring having a window therethrough from a proximal surface to a distal surface; and a second ring adapted to engage the first ring rotatably relative thereto, the second ring comprising a second set of barbs having points protruding generally in a distal direction therefrom, the barbs canted generally in a second circumferential direction with respect to the second ring, each one of the first set having complementary one of the second set to form a pair of barbs, the second ring lockable in a position wherein the point of a one barb of the first set is generally adjacent the point of a complementary barb of the second set, the second ring having a window therethrough from a proximal surface to a distal surface;

wherein in use the first and the second set of barbs are pushed into the skin surrounding the incision, the second ring is rotated to move each one of the complementary pair of barbs adjacent each other, each pair of barbs pinching the skin therebetween, and the second ring is locked to effect anchoring; and wherein the windows in the first and the second ring are adapted to communicate at least partially irrespective of the amount of relative rotation between the first and the second ring, the windows in the first and the second ring for permitting access between the incision and the cylindrical body and to tissue surrounding the incision.

* * * * *